(12) United States Patent
Shen

(10) Patent No.: US 11,631,292 B2
(45) Date of Patent: Apr. 18, 2023

(54) DOOR ACCESS CONTROL METHOD FOR REDUCING PROPAGATION PROBABILITY OF SOME INFECTIOUS DISEASES

(71) Applicant: I-Ting Shen, Tainan (TW)

(72) Inventor: I-Ting Shen, Tainan (TW)

( * ) Notice: Subject to any disclaimer, the term of this patent is extended or adjusted under 35 U.S.C. 154(b) by 0 days.

(21) Appl. No.: 17/528,530

(22) Filed: Nov. 17, 2021

(65) Prior Publication Data

US 2022/0076511 A1 Mar. 10, 2022

Related U.S. Application Data

(62) Division of application No. 16/929,296, filed on Jul. 15, 2020, now Pat. No. 11,250,655.

(30) Foreign Application Priority Data

Jul. 1, 2020 (TW) ................................ 109122266

(51) Int. Cl.
*A61L 2/10* (2006.01)
*G07C 9/00* (2020.01)
(Continued)

(52) U.S. Cl.
CPC ......... *G07C 9/00563* (2013.01); *G01K 13/20* (2021.01); *A61L 2/0047* (2013.01); *A61L 2202/122* (2013.01); *A61L 2202/14* (2013.01)

(58) Field of Classification Search
CPC .......... A61L 2202/14; A61L 2/24; A61L 2/10; A61L 2202/25; A61L 2202/11; A61L 2202/122; A61L 2202/121; A61L 2202/15; A61L 2202/24; A61L 2209/111; A61L 2209/12; A61L 2/0023; A61L 2/16; A61L 2/208; A61L 2/22; A61L 2/26; A61L 2/28; A61L 9/122; A61L 9/14; A61L 9/20; F24F 11/0001; F24F 11/39; F24F 11/46; F24F 11/61; F24F 11/64; F24F 11/72; F24F 2110/50; F24F 2110/64; F24F 2110/65; F24F 2110/70; F24F 2110/74;
(Continued)

(56) References Cited

U.S. PATENT DOCUMENTS 8,382,008 B1 2/2013 Ricciardi et al.
11,250,655 B2 * 2/2022 Shen ..................... G01J 5/0025
(Continued)

*Primary Examiner* — Dionne Pendleton
(74) *Attorney, Agent, or Firm* — Alan D. Kamrath; Karin L. Williams; Mayer & Williams PC

(57) ABSTRACT

A door access control method includes detecting whether a person is intending to pass through a door access control device. Then, it is identified whether a body temperature of the person near the door access control device exceeds a threshold value. The door access control device carries out an unlocking judgment procedure when the body temperature is below the threshold value. The unlocking judgment procedure is not carried out when the body temperature is not below the threshold value. Next, it is identified whether the person is qualified to pass through the door access control device based on the unlocking judgment. The door access control device remains in a locking state when the person is identified as not qualified to pass through the door access control device. The unlocking state is lifted when the person is identified as qualified to pass through the door access control device.

5 Claims, 4 Drawing Sheets

(51) Int. Cl.
*G01K 13/20* (2021.01)
*A61L 2/00* (2006.01)

(58) Field of Classification Search
CPC ............... F24F 2120/10; F24F 2120/20; F24F 2140/60; F24F 3/14; F24F 8/10; F24F 8/22; F24F 3/167; B01D 37/04; B01D 46/002; B01D 46/0028; B01D 46/46; B01D 46/58; B05B 17/0607; B64D 11/02; B64F 5/30; E03D 9/002; G01F 23/00; G01F 23/30; G01K 7/02; G05B 13/041; G05B 15/02; G05B 19/042; G05B 2219/25011; G05B 2219/2614; G05D 7/0629; G16H 40/20; G16H 50/30; Y02B 30/70; Y02B 20/40; G06K 2009/00939; G06K 9/00288; G06K 9/00295; G06K 9/00335; G06K 9/00885; G06K 9/00892; G06K 9/6201; G06K 9/00221; G06K 9/00771; G06Q 10/02; G06Q 20/208; G06Q 20/40145; G06T 2200/24; G06T 2207/10048; G06T 2207/30201; G06T 7/74; G07C 2009/00746; G07C 9/00904; G07C 9/257; G07C 9/27; G07C 9/00563; G07C 9/37; G07C 9/38; H04L 63/0861; H04L 9/3271; H04L 67/10; H05B 47/115; H05B 47/16; G06F 18/22; G06V 10/75; G06V 40/10; G06V 40/15; G06V 40/172; G06V 40/173; G06V 40/20; G06V 40/70

See application file for complete search history.

(56) References Cited

U.S. PATENT DOCUMENTS

| | | |
|---|---|---|
| 2005/0154612 A1 | 7/2005 | Smith et al. |
| 2013/0216438 A1* | 8/2013 | Hill .................. A61L 2/208 422/187 |
| 2014/0255252 A1 | 9/2014 | Stratman et al. |
| 2016/0220716 A1 | 8/2016 | Childress et al. |
| 2020/0372743 A1* | 11/2020 | Miller .................. G06V 40/173 |
| 2021/0011443 A1* | 1/2021 | Mcnamara ........... F24F 11/0001 |
| 2021/0023248 A1 | 1/2021 | Townsend et al. |
| 2021/0252179 A1* | 8/2021 | Grinstead ................. A61L 2/24 |
| 2021/0308311 A1* | 10/2021 | Stewart ..................... A61L 2/24 |

\* cited by examiner

DOOR ACCESS CONTROL METHOD FOR REDUCING PROPAGATION PROBABILITY OF SOME INFECTIOUS DISEASES

CROSS REFERENCE TO RELATED APPLICATION

This is a divisional application of U.S. patent application Ser. No. 16/929,296 filed Jul. 15, 2020.

BACKGROUND OF THE INVENTION

The present invention relates to a door access control method and, more particularly, to a door access control method for reducing propagation probability of some infectious diseases by controlling access to a door and using ultraviolet rays to disinfect bacteria and viruses.

A control device coupled with a door lock is a door access control device that can be used to permit authorized or qualified people to pass through the door access control. A door with such a door access control device generally includes handles. A person can grip and operate a handle to pass through the door while the door access control device is in an unlocked state. However, the person ma carry an infectious disease and, thus, leave bacteria or viruses on the handle of the door, thereby infecting another person operating the handle. Propagation of the infectious disease may, thus, occur.

Another known door access control device utilizes a control device for moving a door. The control device can be an electric motor for driving the door. Although the problem of leaving bacteria or viruses on the handle is eliminated, if the person carrying the infectious disease sneezes or coughs while passing through the door, the bacteria or viruses could still distribute in the space surrounding the door access control device. Other persons intending to pass through the door could still be infected.

BRIEF SUMMARY OF THE INVENTION

In a first aspect, the present invention provides a door access control method for reducing propagation probability of some infectious diseases. The door access control method includes:

detecting whether a person is intending to pass through a door access control device;

identifying whether a body temperature of the person near the door access control device exceeds a threshold value, wherein the door access control device carries out an unlocking judgment procedure when the body temperature of the person is below the threshold value, and wherein the unlocking judgment procedure is not carried out when the body temperature of the person is not below the threshold value; and identifying whether the person is qualified to pass through the door access control device based on a result of the unlocking judgment procedure, wherein the door access control device remains in a locking state when the person is identified as not qualified to pass through the door access control device, and wherein the unlocking state of the door access control device is lifted when the person is identified as qualified to pass through the door access control device.

In the door access control method according to the present invention, after the person has used the door access control device, ultraviolet rays are used to eliminate or reduce the number of viruses and bacteria possibly residing on the first and/or second handle and in the first and/or second disinfection areas. Thus, the possibility of infection due to passage of an uncertain person through the door access control device can be reduced.

In an example, the door access control method further includes identifying whether a primary disinfection operation is completed before lifting the unlocking state of the door access control device. The primary disinfection operation starts during the unlocking judgment procedure and is identified whether completed or not. The locking state of the door access control device is not lifted before the primary disinfection operation is completed.

In an example, the door access control method further includes:

detecting whether the person has left the first and second disinfection areas while the door access control device is in an unlocking state, wherein a secondary disinfection operation is carried out to disinfect the door access control device and a disinfection area around the door access control device when the person has left the first and second disinfection areas and is identified whether completed or not, and wherein the second disinfection operation is not carried out when the person is in the first or second disinfection area;

continuing the secondary disinfection area until it is completed;

detecting whether any person is in the first or second disinfection area; and terminating the secondary disinfection operation when completed or any person is in the first or second disinfection area.

In an example, the disinfection area has an outer edge spaced from the door access control device by a spacing not larger than 10 m.

In an example, the primary disinfection operation is considered as complete after proceeding for about 5-15 seconds, and the secondary disinfection operation is considered as complete after proceeding for about 10-30 minutes.

In an example, the secondary disinfection operation includes disinfecting the disinfection area with at least one first disinfection device in the first disinfection area and at least one second disinfection device in the second disinfection area and includes illuminating a first handle of the door access control device with a first handle disinfection device for 1-3 minutes.

In an example, the primary disinfection operation includes illuminating a first handle of the door access control device with a first handle disinfection device for a period of time.

In a second aspect, the present invention provides a door access control method for educing propagation probability of some infectious diseases. The door access control method includes:

detecting whether a person is intending to pass from an unrestricted disinfection area through a door access control device to a restricted disinfection area;

identifying whether a body temperature of the person near the door access control device exceeds a threshold value, wherein the door access control device carries out an unlocking judgment procedure when the body temperature of the person is below the threshold value, and wherein the unlocking judgment procedure is not carried out when the body temperature of the person is not below the threshold value;

identifying whether the person is qualified to pass through the door access control device based on a result of the unlocking judgment procedure, wherein the door access control device remains in a locking state preventing the person from passing from the unrestricted disinfection area through the door access control device to the restricted disinfection area when the person is identified as not qualified to pass through the door access control device, and wherein the unlocking state of the door access control device is lifted to permit the person to pass from the unrestricted disinfection area through the door access control device to the restricted disinfection area when the person is identified as qualified to pass through the door access control device;

detecting whether a person is intending to pass from the restricted disinfection area through the door access control device to the unrestricted disinfection area; and deciding whether to start a secondary disinfection operation, wherein the secondary disinfection operation is not carried out when any person is in the restricted or unrestricted disinfection area, and wherein the secondary disinfection operation is carried out when the person passing from the restricted area to the unrestricted disinfection area has left the unrestricted disinfection area, wherein the secondary disinfection area continues until it is completed while no person is in the restricted disinfection area and the unrestricted disinfection area, and wherein the secondary disinfection operation is terminated when completed or any person enters the restricted disinfection area or the unrestricted disinfection area.

In an example, the door access control method further includes identifying whether a primary disinfection operation is completed before lifting the unlocking state of the door access control device. The primary disinfection operation starts during the unlocking judgment procedure acid is identified whether completed or not. The locking state of the door access control device is not lifted before the primary disinfection operation is completed.

In an example, the primary disinfection operation includes illuminating a first handle of the door access control device with a first handle disinfection device for a period of time.

In an example, the door access control method further includes detecting whether the person passing from the unrestricted disinfection area to the restricted disinfection area has left the restricted disinfection area. The secondary disinfection operation is not carried out when the person is still in the restricted disinfection area. The secondary disinfection operation is carried out when the person has left the restricted disinfection area.

In an example, the primary disinfection operation is considered as complete after proceeding for about 5-15 seconds, and the secondary disinfection operation is considered as complete after proceeding for about 10-30 minutes.

In an example, the secondary disinfection operation includes disinfecting the disinfection area with at least one first disinfection device in the first disinfection area and at least one second disinfection device in the second disinfection area and includes illuminating a first handle of the door access control device with a first handle disinfection device for 1-3 minutes.

The present invention will become clearer in light of the following detailed description of illustrative embodiments of this invention described in connection with the drawings.

Figure 1:
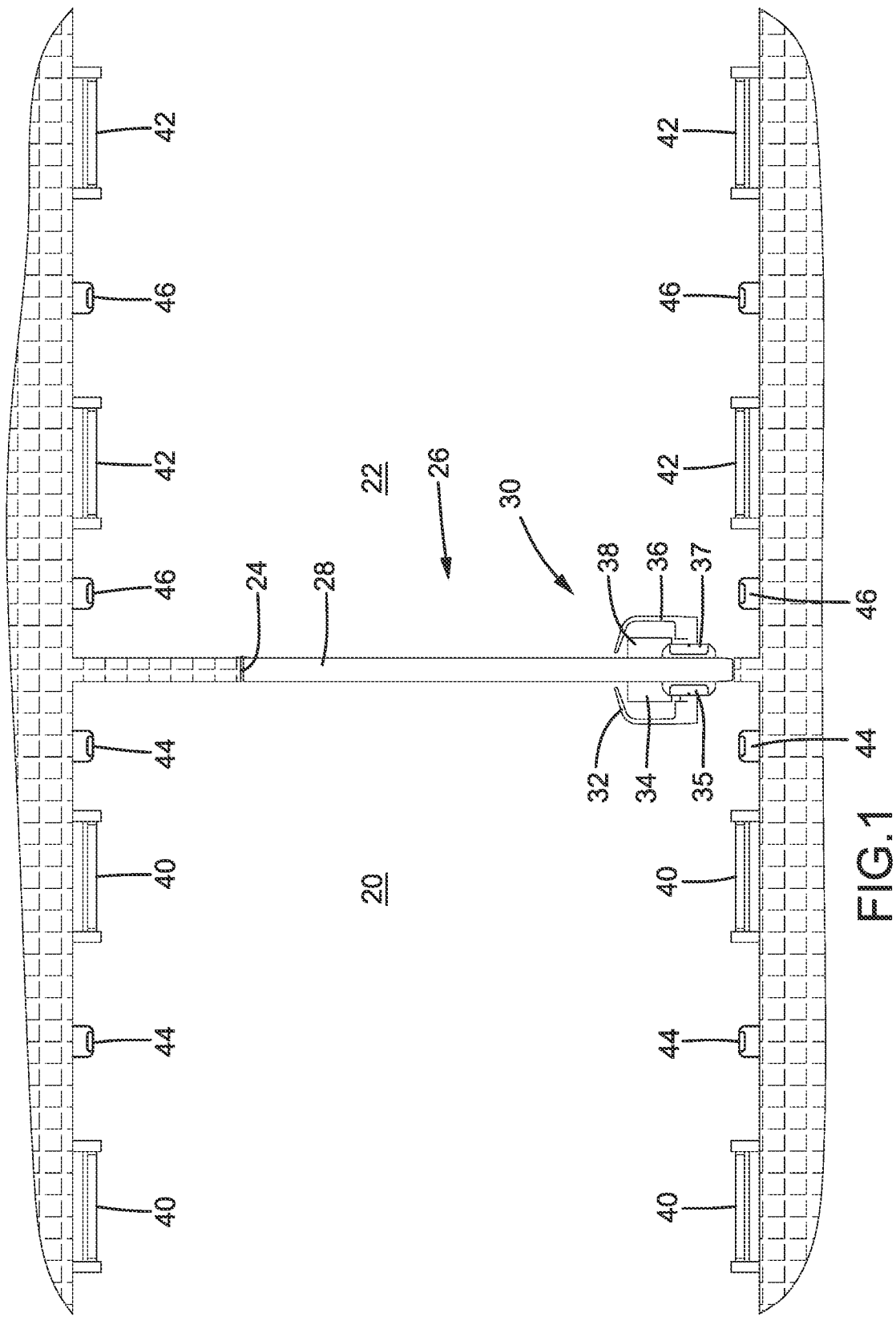
FIG. 1 is a diagrammatic view of a door access control device for carrying out of a door access control method for reducing propagation probability of some infectious diseases according to the present invention.

All figures are drawn for ease of explanation of the basic teachings of the present invention only; the extensions of the figures with respect to number, position, relationship, and dimensions of the parts to form the embodiments will be explained or will be within the skill of the art after the following teachings of the present invention have been read and understood. Further, the exact dimensions and dimensional proportions to conform to specific force, weight, strength, and similar requirements will likewise be within the skill of the art after the following teachings of the present invention have been read and understood.

Where used in the various figures of the drawings, the same numerals designate the same or similar parts. Furthermore, when the terms "first", "second", "area", "indoor", "outdoor", and similar terms are used herein, it should be understood that these terms have reference only to the structure shown in the drawings as it would appear to a person viewing the drawings and are utilized only to facilitate describing the invention.

DETAILED DESCRIPTION OF THE INVENTION

The present invention relates to a door access control method for reducing propagation probability of some infectious diseases (hereinafter referred to as "door access control method") based on detecting a body temperature of users and/or passage conditions of a door access control device as well as disinfection and sterilization on the door access control device and its ambience. The term "some infectious diseases" used herein includes diseases that can cause fevers after infection or other infectious diseases (such as flu, covid-19, SARS, etc.) transmitted by droplets, air, fecal-oral route, aerosols, etc.

Figure 2:
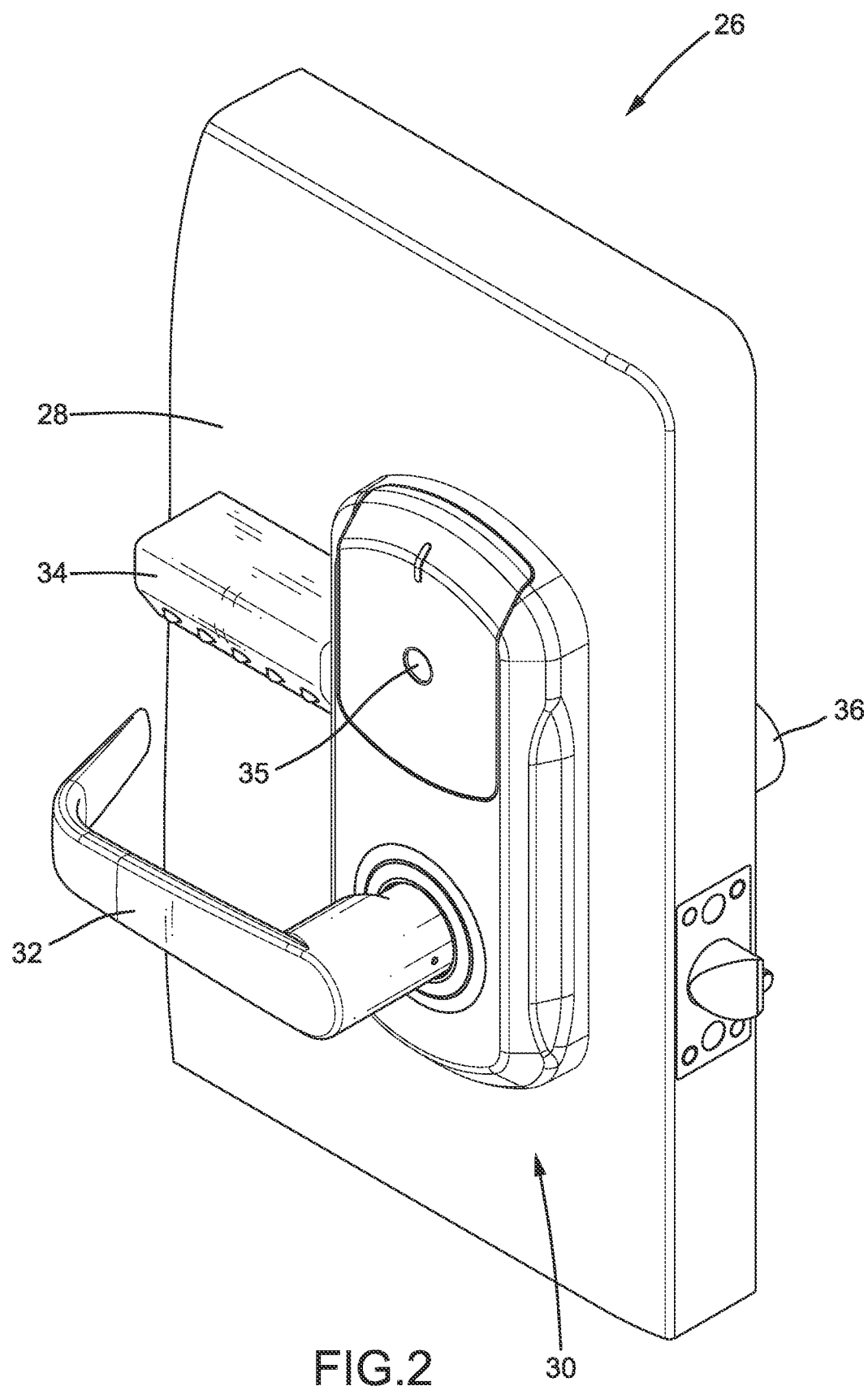
FIG. 2 is a perspective view of the door access control device of FIG. 1.

With reference to FIGS. 1 and 2, the door access control method according to the present invention can be carried out through cooperation of a door access control device 26. The door access control device 26 is disposed in a passageway 24 between a first space (such as an outdoor space) and a second space (such as an indoor space). As used herein, the term "disinfection area" refers to an annular area centered at the passageway 24 and having an outer edge spaced from the passageway 24 by a spacing not larger than 10 m. Thus, a first disinfection area 20 can be an annular area in the first space spaced from the passageway 24 by a spacing not larger than 10 m. A second disinfection area 22 can be an annular area in second first space spaced from the passageway 24 by a spacing not larger than 10 m. The door access control device 26 includes a door 28 mounted in the passageway 24 for opening and closing the passageway 24. The door access control device 26 further includes a control device 30 coupled to the door 28. The control device 30 includes a first handle 32 located in the first disinfection area 20 and a first handle disinfection device 34 aligned with the first handle 32. The control device 30 further includes a second handle 36 located in the second disinfection area 22 and a second handle disinfection device 38 aligned with the second handle 36. Furthermore, the control device 30 includes a first body temperature measurement device 35 facing the first disinfection area 20 and a second body temperature measurement device 37 facing the second disinfection area 22. In an example, the control device 30 is in the form of a door lock, such as an electronic door lock or a mechanic door lock.

The first handle 32 and the second handle 36 can be used to push open the door 28 (when the control device 30 is set in an unlocking state) or close the door 28. When the door 28 is opened, persons are permitted to move from the first disinfection area 20 (the first space) through the passageway 24 to the second disinfection area 22 (the second space) or to move from the second disinfection area 22 (the second space) through the passageway 24 to the first disinfection area 20 (the first space). In an example, the first handle disinfection device 34 and the second handle disinfection device 38 can be devices for generating ultraviolet rays having a wavelength ranging from 100 nm to 280 am, preferably 245 nm. The first handle disinfection device 34 and the second handle disinfection device 38 can be disposed to directly radiate the first handle 32 and the second handle 36. The first body temperature measurement device 35 and the second body temperature measurement device 37 can be infrared thermal imaging cameras.

A plurality of first disinfection devices 40 and a plurality of first sensors 44 are disposed in the first disinfection area 20 and are connected to the control device 30. A plurality of second disinfection devices 42 and a plurality of second sensors 46 are disposed in the second disinfection area 22 and are connected to the control device 30. In an example, the plurality of first handle disinfection devices 34 and the plurality of second handle disinfection devices 38 can be devices for generating ultraviolet rays having a wavelength ranging from 100 nm to 280 nm, preferably 245 nm. The plurality of first sensors 44 and the plurality of second sensors 46 can be infrared sensors. Each of the plurality of first sensors 44 is used to detect presence of a person in the first disinfection area 20. Each of the plurality of second sensors 46 is used to detect presence of a person in the second disinfection area 22.

Figure 3:
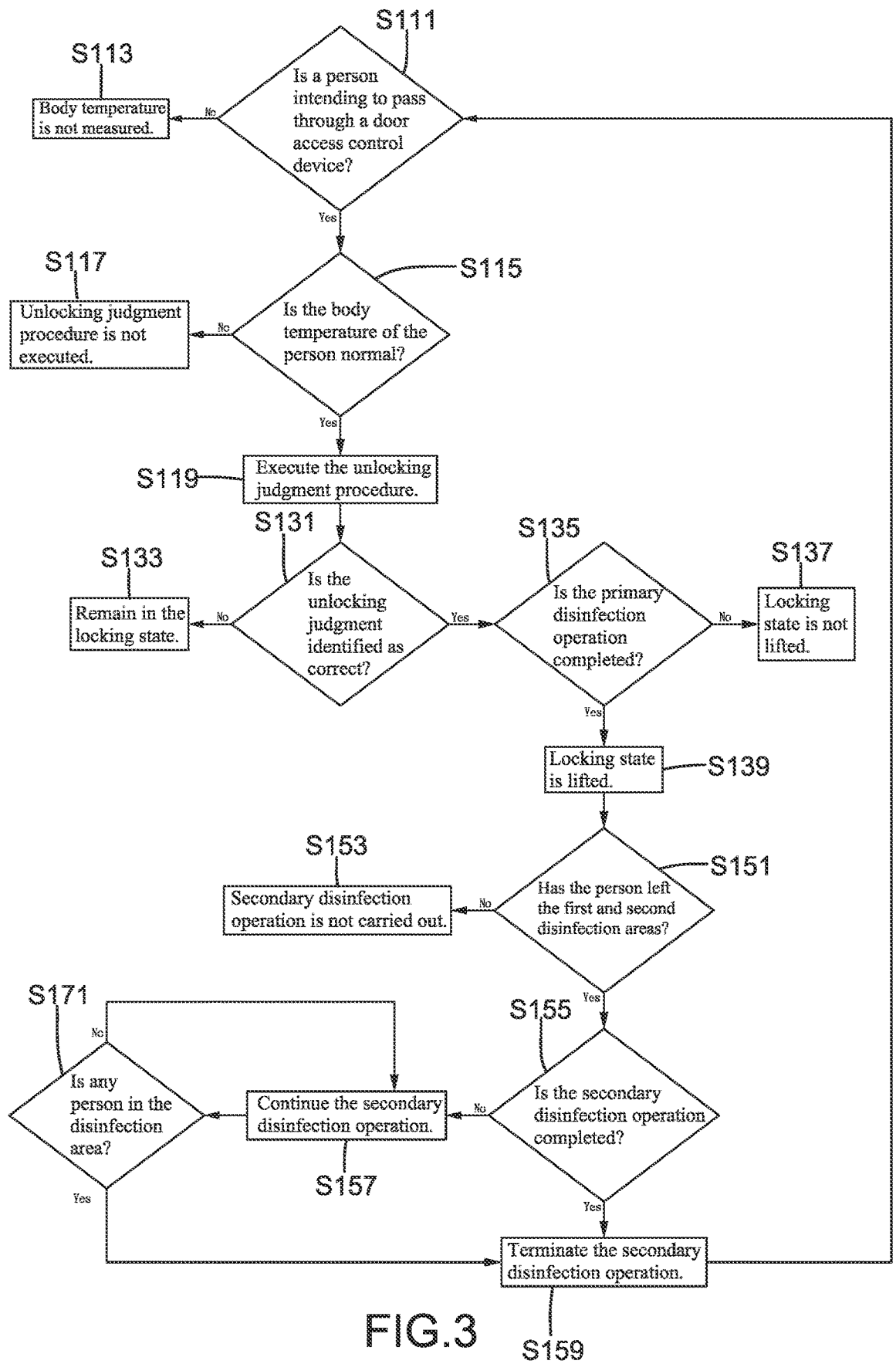
FIG. 3 is a flowchart illustrating a first embodiment of the door access control method for reducing propagation probability of some infectious diseases according to the present invention.

FIG. 3 shows a flowchart illustrating a first embodiment of the door access control method for reducing propagation probability of some infectious diseases according to the present invention. The first embodiment of the door access control method can be carried out indoors or outdoors. When a person intends to pass from the first disinfection area 20 into the second disinfection area 22 through the passageway 24 or to pass from the second disinfection area 22 into the first disinfection area 20 through the passageway 24, the control device 30 proceeds with unlocking judgment and will unlock to permit passage only when the person is identified as qualified.

The first embodiment of the door access control method includes detecting whether a person is intending to pass through the door access control device 26 (step S111). Namely, in step S111, it is detected that whether a person is near the door access control device 26. In a case that the control device 30 uses a wireless communication technique (such as Bluetooth) to communicate with a smart mobile device of the person, it is identified that a person is near the door access control device 26 when the person is located in a communication range of the wireless communication technique. In another case that the control device 30 uses a door access control technique, such as radio frequency identification (RFID) technique or near field communication (NFC), it is identified that a person is near the door access control device 26 when the person places a door access card near the control device 30 to proceed with induction.

When it is identified that no person is near the door access control device 26, body temperature measurement is not conducted (S113). For example, when neither a smart mobile device of a person is in communication with the control device 30 nor a person places a door access card near the control device 30, it is identified that there is no person near the door access control device 26. In this state, the first and second body temperature measurement devices 35 and 37 are not activated to measure the body temperature.

In step S115, before the person passing through the door access control device 26, it is identified whether the body temperature of the person near the door access control device 26 is too high (namely, exceeds a threshold value). For example, when a smart mobile device of a person is in communication with the control device 30 or a person places a door access card near the control device 30, it is identified that a person is near the door access control device 26. In this state, the first body temperature measurement device 35 or the second body temperature measurement device 37 measures the body temperature of the person. It is noted that when the control device 30 detects that the smart mobile device of the person is located in the first disinfection area 20 and is in communication with the control device 30 or when the person in the first disinfection area 20 uses a door access card to induct with the control device 30, the control device 30 activates the first body temperature measurement device 35 to measure the body temperature of the person in the first disinfection area 20. When the body temperature is higher than or equal to 37° C. it is identified that body temperature of the person is too high. On the other hand, when the body temperature is lower than 37° C. (the threshold value), it is identified that the body temperature of the person is normal. Likewise, when the control device 30 detects that the smart mobile device of the person is located in the second disinfection area 22 and is in communication with the control device 30 or when the person in the second disinfection area 22 uses a door access card to induct with the control device 30, the control device 30 activates the second body temperature measurement device 37 to measure the body temperature of the person in the second disinfection area 22. When the body temperature is higher than or equal to 37° C. (the threshold value), it is identified that the body temperature of the person is too high. On the other hand, when the body temperature is lower than 37° C., it is identified that the body temperature of the person is normal.

When the body temperature of the person is too high, the door access control device 26 does not execute an unlocking procedure (step S117), and the person cannot pass through the door access control device 26, in a case that the body temperature of the person measured by the first body temperature measurement device 35 is not lower than 37° C. while the smart mobile device of the person is in communication with the control device 30 or the person uses the door access card to induct with the control device 30, the control device 30 still does not execute an unlocking judgment procedure even if the person is qualified or authorized to pass through the door 28. Thus, the person with a body temperature not lower than 37° C. is not permitted to pass from the first disinfection area 20 through the door access control device 26 into the second disinfection area 22. Likewise, when the body temperature of the person measured by the second body temperature measurement device 37 in the second disinfection area 22 is not lower than 37° C. while the smart mobile device of the person is in communication with the control device 30 or the person uses the door access card to induct with the control device 30, the control device 30 still does not execute the unlocking judgement procedure even if the person is qualified or authorized to pass through the door 28. Thus, the person with a body temperature not lower than 37° C. is not permitted to pass from the second disinfection area 22 through the door access control device 26 into the first disinfection area 20.

When the body temperature of the person is normal, the door access control device 26 executes the unlocking judgment procedure (step S119). In a case that the body temperature of the person measured by the first body temperature measurement device 35 in the first disinfection area 20 is lower than 37° C., the control device 30 executes the unlocking judgment procedure while the smart mobile device of the person is in communication with the control device 30 or the person uses the door access card to induct with the control device 30. Likewise, in another case that the body temperature of the person measured by the second body temperature measurement device 37 in the second disinfection area 22 is lower than 37° C., the control device 30 executes the unlocking judgment procedure while the smart mobile device of the person is in communication with the control device 30 or the person uses the door access card to induct with the control device 30.

In step S131, it is identified whether the person is qualified to pass through the door access control device 26. When the body temperature of the person is normal, the control device 30 identifies whether the person is qualified or authorized to pass through the door access control device 26. With the smart mobile device in communication with the control device 30, the control device 30 reads an identification information (such as a biological feature, a password, or an activation key) from the smart mobile device and judges whether the identification information is authorized to pass through the door access control device 26. In the case of a door access card which is placed by the person in a position near the control device 30, the control device 30 reads an identification information in the door access card and identifies whether the identification information in the door access card is authorized to pass through the door access control device 26.

When it is identified that the person is not qualified to pass through the door access control device 26, the door access control device 26 remains in the locking state to prevent the person from passing through the door access control device 26 (see step S133). For example, when the control device 30 identifies the identification information outputted from the smart mobile device or the door access card of the person as incorrect (e.g., the identification information of the smart mobile device or the door access card is not on a list of authenticated identification informations related to authorized persons permitted to pass through the door access control device 26), the control device 30 remains in the locking state.

While executing the unlocking judgement procedure, a primary disinfection operation is carried out and identified whether completed or not (step S135). Specifically, the primary disinfection operation starts while the control device 30 executes the unlocking judgement procedure. During execution of the primary disinfection operation, the first handle disinfection device 34 and/or the second handle disinfection device 38 of the control device 30 operate to generate ultraviolet rays that radiate the first handle 32 and/or the second handle 36 for 5-15 seconds. For example, during execution of the primary disinfection operation, the first handle disinfection device 34 and the second handle disinfection device 38 operate to generate ultraviolet rays that radiate the first handle 32 and the second handle 36 for 10 seconds. When the first handle disinfection device 34 and the second handle disinfection device 38 generate the ultraviolet rays for a period of time less than 10 seconds, it is identified that the primary disinfection operation is not complete. On the other hand, when the first handle disinfection device 34 and the second handle disinfection device 38 generate the ultraviolet rays for a period of time not shorter than 10 seconds, it is identified that the primary disinfection operation is complete.

When the primary disinfection operation is not complete, the door access control device 26 does not lift the locking state (step S137). Specifically, before the ultraviolet rays of the first handle disinfection device 34 and the second handle disinfection device 38 extinguish (with no UV rays present), the control device 30 still does not execute the unlocking operation even if the control device 30 identifies the identification information of the smart mobile device or the door access card as correct (namely, the identification information matches with one of a plurality of authorized identification informations).

When the person is identified as qualified to pass through the door access control device 26, the door access control device 26 lifts the locking state (step S139). Specifically, when the ultraviolet rays of the first handle disinfection device 34 and the second handle disinfection device 38 extinguish and the control device 30 identifies the identification information of the smart mobile device or the door access card as correct, the control device 30 is set to an unlocking state to permit the person to pass from the first disinfection area 20 through the door access control device 26 to the second disinfection area 22 or to pass from the second disinfection area 22 through the door access control device 26 to the first disinfection area 20.

In step S151, it is detected whether the person has passed through the door access control device 26 in the unlocking state by checking whether the person has left the first disinfection area 20 and the second disinfection area 22. In a case that the person in the first disinfection area 20 lifts the locking state of the control device 30, when the control device 30 receives a signal from each of the plurality of first sensors 44 indicating that the person originally in the first disinfection area 20 is no longer in the first disinfection area 20 and then receives another signal from each of the plurality of second sensors 46 indicating that the person was in the second disinfection area 22 but now no longer in the second disinfection area 22 (namely, the person has left the first and second disinfection areas 20 and 22), the control device 30 identifies that the person has passed through the door access control device 26. Likewise, when the control device 30 receives a signal from each of the plurality of second sensors 46 indicating that the person originally in the second disinfection area 22 is no longer in the second disinfection area 22 and then receives another signal from each of the plurality of first sensors 44 indicating that the person was in the first disinfection area 20 but now is not in the first disinfection area (namely, the person has left the first and second disinfection areas 20 and 22), the control device 30 identifies that the person has passed through the door access control device 26. Given that the control device 30 is in the unlocking state, when each of the plurality of first sensors 44 detects that a person intending to pass from the first disinfection area 20 to the second disinfection area 22 is still in the first disinfection area 20, the control device 30 identifies that the person has not passed through the door access control device 26. Likewise, given that the control device 30 is in the unlocking state, when each of the plurality of second sensors 46 detects that a person intending to pass from the second disinfection area 22 to the first disinfection area 20 is still in the second disinfection area 22, the control device 30 identifies that the person has not passed through the door access control device 26.

Before the person passes through the door access control device 26, a secondary disinfection operation is not carried out (step S153). Specifically, when the control device 30 is set to the locking state and receives a signal indicating that the person has not passed through the door access control device 26 (e.g., each of the plurality of first sensors 44 detects that the person is still in the first disinfection area 20 or each of the plurality of second sensors 46 detects that the person is still in the second disinfection area 22), the control device 30 does not activate the first and second disinfection devices 40 and 42 and the first and second handle disinfection devices 34 and 38.

After the person passes through the door access control device 26, the secondary disinfection operation is activated to disinfect the door access control device 26 and the area around the door access control device 26, and it is detected whether the secondary disinfection operation is complete (step S155). Specifically, the secondary disinfection operation is that, when the person has passed through the door access control device 26 and when no person is present in the first and second disinfection areas 20 and 22, the control device 30 activates the first and second handle disinfection devices 34 and 38 and the first and second disinfection devices 40 and 42 to generate ultraviolet rays to illuminate the first and second handles 32 and 36 and the first and second disinfection areas 20 and 22. Given there is no person in the first or second disinfection area 20 or 22, the secondary disinfection operation (the radiation time by ultraviolet rays) is preferably 10-30 minutes. The disinfection time of the secondary disinfection operation can be determined according to the area of the ambience of the door access control device 26. For example, the disinfection time of the secondary disinfection operation can be 10 minutes for smaller first and second disinfection areas 20 and 22 or 30 minutes for larger first and second disinfection areas 20 and 22.

The secondary disinfection operation continues until it is executed completely (step S157). For example, the secondary disinfection operation is set to illuminate ultraviolet rays for 10 minutes (namely, the ultraviolet ray source operates for 10 minutes). Given that the secondary disinfection operation is started and that no person is in the first and second disinfection areas 20 and 22, when the first and second disinfection areas 20 and 22 and the first and second handles 32 and 36 are irradiated by ultraviolet rays for less than 10 minutes, it is identified that the secondary disinfection operation is complete. The first and second disinfection devices 40 and 42 and the first and second handle disinfection devices 34 and 38 continues to generate ultraviolet rays.

In step S171, it is detected whether any person is in the disinfection area. Specifically, the wavelengths of the ultraviolet rays generated by the first and second disinfection devices 40 and 42 and the first and second handle disinfection devices 34 and 38 are in a range of 100-280 nm, which is not suitable to directly radiate the human body. Furthermore, during the secondary disinfection operation, the first and second disinfection devices 40 and 42 widely radiate the first and second disinfection areas 20 and 22, in a case that a person enters the first or second disinfection area 20, 22 and will be directly illuminated by the ultraviolet rays with a wavelength of 100-280 nm the plurality of first and second sensors 44 and 46 must be used to detect whether any person enters the first or second disinfection area 20 or 22 to avoid injury to persons.

After the secondary disinfection operation is complete or a person is in the disinfection area, the secondary disinfection operation is terminated (step S159). Given the secondary disinfection operation is set to 10 minutes, the secondary disinfection operation is complete when the ultraviolet rays generated by the first and second disinfection devices 40 and 42 and the first and second handle disinfection devices 34 and 38 have radiated the first and second disinfection areas 20 and 22 and the first and second handles 32 and 36 for 10 minutes. Then, the control device 30 stops operation of the first and second disinfection devices 40 and 42 and the first and second handle disinfection devices 34 and 38 to thereby turn off all ultraviolet ray sources.

In a case that the second disinfection operation is not complete, when a person enters the first or second disinfection area 20 or 22, the second disinfection operation is terminated to stop the operation of the first and second disinfection devices 40 and 42 and the first and second handle disinfection devices 34 and 38 to thereby turn off all ultraviolet ray sources. For example, given the disinfection operation is set to 10 minutes, when a person intends to pass from the first disinfection area 20 through the door access control device 26 to the second disinfection area 22 at the $7^{th}$ minute after the disinfection operation starts, the control device 30 immediately stops operation of the first and second disinfection devices 40 and 42 and the first and second hand disinfection devices 34 and 38 to turn off the ultraviolet rays as soon as each of the plurality of first sensors 44 detects the person. Then, the procedure returns to step S111. Namely, the person could enter the first or second disinfection area 20 or 22 during the secondary disinfection operation by mistake or on purpose. Thus, after terminating the ongoing secondary disinfection operation, the control device 30 identifies whether any person intends to pass through the door access control device 26 based on intercommunication between the smart mobile device of the person and the control device 30 or based on induction between the door access card of the person and the control device 30. If a person enters the first or second disinfection area 20 or 22 by mistake during the secondary disinfection operation, the smart mobile device or the door access card of the person will not communicate or induct with the control device 30. After the person leaves the first or second disinfection area 20 or 22, the secondary disinfection operation is resumed to complete the rest of the radiation time.

Figure 4:
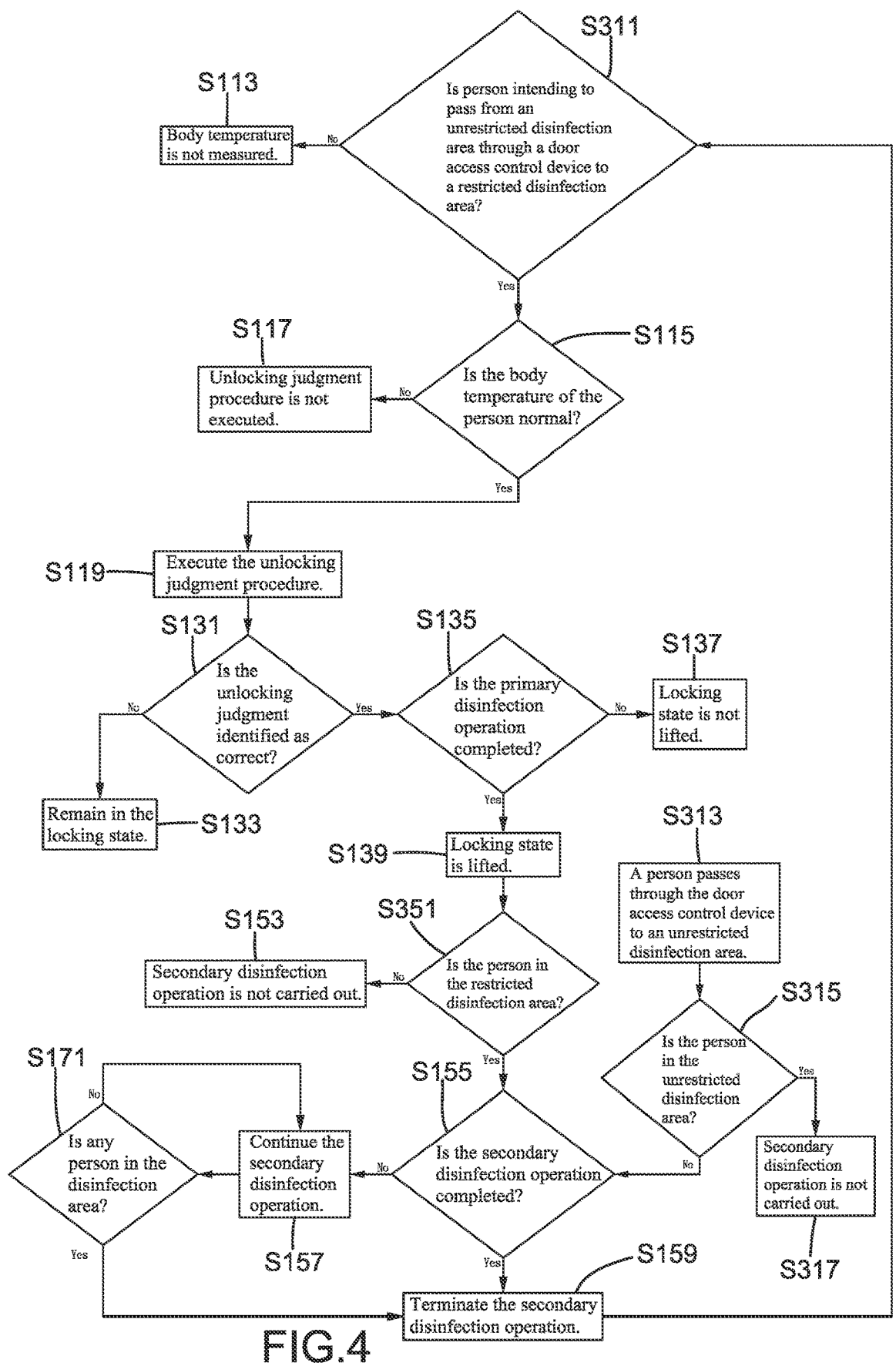
FIG. 4 is a flowchart illustrating a second embodiment of the door access control method for reducing propagation probability of some infectious diseases according to the present invention.

In the embodiment shown in FIG. 3 illustrating passage from the first disinfection area 20 through the door access control device 26 to the second disinfection area 22 or passage from the second disinfection area 22 through the door access control device 26 to the first disinfection area 20, the locking state of the control device 30 is lifted to permit passage of a person only when the body temperature of the person is not too high and the unlocking judgement is identified as correct. Nevertheless, the door access control method according to the present invention can be used in an environment including a restricted area (e.g., an indoor space) and an unrestricted area (e.g., an outdoor space). With reference to FIGS. 1 and 4, the first disinfection area 20 is defined as an unrestricted disinfection area (an outdoor space), and the second disinfection area 22 is defined as a restricted disinfection area (an indoor space), in this state, the body temperature of the person has to be measured to execute the unlocking judgement procedure when the person intends to pass from the unrestricted disinfection area (the first disinfection area 20) through the door access control device 26 to the restricted disinfection area (the second disinfection area 22). On the other hand, it is not necessary to execute the measure the body temperature of the person nor necessary to execute the unlocking judgement procedure when the person intends to pass from the restricted disinfection area (the second disinfection area 22) through the door access control device to the unrestricted disinfection area (the first disinfection area 20).

The first embodiment illustrated in FIG. 3 differs from the second embodiment illustrated in FIG. 4 by the judgement of passing from the first disinfection area 20 through the door access control device 26 to the second disinfection area 22 or vise versa. Specifically, with reference to FIG. 4, the second embodiment of the door access control method according to the present invention includes detecting whether a person is intending to pass through the door access control device 26 (step S311). Namely, in step S311, it is detected that whether a person is in the unrestricted disinfection area (the first disinfection area 20) near the door access control device 26. In a case that the control device 30 uses a wireless communication technique (such as Bluetooth) to communicate with a smart mobile device of the person, it is identified that a person is in the unrestricted disinfection area (the first disinfection area 20) when the person is located in a communication range of the wireless communication technique (namely, the spacing between the smart mobile device of the person and the control device 30 is within the communication range of the wireless communication technique). In another case that the control device 30 uses a door access control technique, such as radio frequency identification (RFID) technique or near field communication (NFC), when the person is in the unrestricted disinfection area (the first disinfection area 20), when each of the plurality of first sensors 44 detects the person, and when the person places a door access card near the control device 30 to proceed with induction, it is identified that a person is intending to pass from the unrestricted disinfection area (the first disinfection area 20) through the door access control device 26 to the restricted disinfection area (the second disinfection area 22).

When it is identified that no person is in the unrestricted disinfection area (the first disinfection area 20), body temperature measurement is not conducted (S113). When the control device 30 is in the locking state and no person is intending to pass from the unrestricted disinfection area (the first disinfection area 20) through the door access control device 26 to the restricted disinfection area (the second disinfection area 22), the control device 30 does not activate the first body temperature measurement device 35 to operate. In another case that the person is intending to pass from the restricted disinfection area (the second disinfection area 22) through the door access control device 26 to the unrestricted disinfection area (the first disinfection area 20), the control device 30 measure the body temperature of the person.

In step S115, before the person passing through the door access control device 26, it is identified whether the body temperature of the person near the door access control device 26 is too high (namely, exceeds a threshold value). For example, when a person intends to pass from the unrestricted disinfection area (the first disinfection area 20) through the door access control device 26 to the restricted disinfection area (the second disinfection area 22), the first body temperature measurement device 35 of the door access control device 26 measures the body temperature of the person. When the body temperature of the person is not lower than 37° C., it is identified that the body temperature is too high. When the body temperature of the person is lower than 37° C. it is identified that the body temperature is normal.

When the body temperature of the person is too high, the door access control device 26 does not execute the unlocking judgment procedure (step S117), and the person cannot pass through the door access control device 26 to the restricted disinfection area (the second disinfection area 22). In the second embodiment illustrated in FIG. 4, the body temperature of the person is measured only when the person intends to pass from the unrestricted disinfection area (the first disinfection area 20) through the door access control device 26 to the restricted disinfection area (the second disinfection area 22). In a case that the body temperature of the person is not lower than 37° C., the control device 30 identifies the body temperature of the person is too high. In this case, even if the smart mobile device of the person is in communication with the control device 30 or the person uses the door access card to induct with the control device 30, the control device 30 still does not execute the unlocking judgment procedure.

When the body temperature of the person is normal, the door access control device 26 executes the unlocking judgment procedure (step S119). In the second embodiment, only when the person intends to pass from the unrestricted disinfection area (the first disinfection area 20) through the door access control device 26 to the restricted disinfection area (the second disinfection area 22) and when the body temperature of the person measured by the first body temperature measurement device 35 in the unrestricted disinfection area (the first disinfection area 20) is lower than 37° C., the control device 30 executes the unlocking judgment procedure while the smart mobile device of the person is in communication with the control device 30 or the person uses the door access card to induct with the control device 30.

In the second embodiment illustrated in FIG. 4, the steps S131, S133, and S139 are identical to the steps S131, S133, and S139 described in the first embodiment illustrated in FIG. 3 and are, therefore, not described again to avoid redundancy.

In step S351, it is identified whether the person passing through the door access control device 26 has left the restricted disinfection area (the second disinfection area 22). If yes, the secondary disinfection operation is carried out. If not (the person passing through the door access control device 26 is still in the restricted disinfection area), the secondary disinfection operation is not carried out.

In step S313, it is detected whether a person is intending to pass from the restricted disinfection area (the second disinfection area 22) through the door access control device 26 to the unrestricted disinfection area (the first disinfection area 20). If yes, since the second disinfection area 22 is an indoor space, it is not necessary to measure the body temperature of the person, nor the unlocking judgment procedure by the control device 30 is required. Thus, the person can directly operate the second handle 36 to set the control device 30 to the unlocking state and then opens the door 28 to pass from the restricted disinfection area (the second disinfection area 22) through the door access control device 26 to the unrestricted disinfection area (the first disinfection area 20).

In step S315, it is detected whether the person has left the unrestricted disinfection area 20. When the person is not in the unrestricted disinfection area 20, the secondary disinfection operation is carried out. Specifically, when the person that has passed through the door access control device 26 is still in the unrestricted disinfection area, the secondary disinfection operation is not carried out (S317). This avoids the ultraviolet rays generated during the secondary disinfection operation from directly illuminating the human body.

When any person is in the first disinfection area 20 (the unrestricted disinfection area) or the second disinfection area 22 (the restricted disinfection area), the secondary disinfection operation S317 is not carried out. To avoid the ultraviolet rays from directly illuminating the human body, the secondary disinfection operation is not carried out when the person passing from the second disinfection area 22 (the restricted disinfection area) through the door access control device 26 to the first disinfection area 20 (the unrestricted disinfection area) is still in the first disinfection area 20 or when another person enters the second disinfection area 22. Namely, in this state, the first and second disinfection devices 40 and 42 and the first and second handle disinfection devices 34 and 38 do not operate.

When the person has passed through the door access control device 26 and when no person is in the first and second disinfection areas 20 and 22, the secondary disinfection operation is carried out to disinfect the door access control device 26 and the first and second disinfection areas 20 and 22, and it is detected whether the secondary disinfection operation is complete (step S155). Specifically, after the secondary disinfection operation is activated, the first and second disinfection devices 40 and 42 generate ultraviolet rays to illuminate the first and second disinfection areas 20 and 22, and the first and second handle disinfection devices 34 and 38 generate ultraviolet rays to illuminate the first and second handles 32 and 36.

In the second embodiment illustrated in FIG. 4, the steps S157, S159, and S171 are identical to the steps S157, S159, and S171 described in the first embodiment illustrated in FIG. 3 and are, therefore, not described again to avoid redundancy.

In the door access control method according to the present invention, after the person has passed through the door access control device 26, ultraviolet rays are used to eliminate or reduce the number of viruses and bacteria possibly left on the first and/or second handle 32, 36 and in the first and/or second disinfection areas 20 and 22. Thus, the possibility of infection due to passage of an uncertain person through the door access control device 26 can be reduced.

In the door access control method according to the present invention, after the person has used the door access control device 26, the first and second disinfection devices 40 and 42 are activated to generate ultraviolet rays to illuminate the first and second disinfection areas 20 and 22 only when no person is in the first and second disinfection areas 20 and 22. Thus, the spread of the contagious diseases can be reduced while avoiding the human body from being harmed.

In the door access control method according to the present invention, the first and second handle disinfection devices 34 and 38 and the first and second disinfection devices 40 and 42 provide ultraviolet ray sources to generate ultraviolet rays to thereby automatically radiate the first and second handles 32 and 36 and the first and second disinfection areas 20 and 22 while cooperating with the door access control, which is relatively convenient in use.

While the control device 30 is executing the unlocking judgment procedure, the first and second handle disinfection devices 34 and 38 are activated to generate ultraviolet rays to illuminate the first and second handles 32 and 36. In the case that the unlocking judgment is identified as correct and the person manually operates the first handle 32 or the second handle 36 to open the door 28, the risk of infection of the contagious diseases through the first or second handle 32 or 36 can be avoided.

Now that the basic teachings of the present invention have been explained, many extensions and variations will be obvious to one having ordinary skill in the art. For example, the control device 30 can be a device other than locks, such as a driving device (e.g., a motor device) for opening or closing the door 28.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

The invention claimed is:

1. A door access control method comprising:

detecting whether a person is intending to pass from an unrestricted disinfection area through a door access control device to a restricted disinfection area;

identifying whether a body temperature of the person near the door access control device exceeds a threshold value, wherein the door access control device carries out an unlocking judgment procedure when the body temperature of the person is below the threshold value, and wherein the unlocking judgment procedure is not carried out when the body temperature of the person is not below the threshold value;

identifying whether the person is qualified to pass through the door access control device based on a result of the unlocking judgment procedure, wherein the door access control device remains in a locking state preventing the person from passing from the unrestricted disinfection area through the door access control device to the restricted disinfection area when the person is identified as not qualified to pass through the door access control device, and wherein the unlocking state of the door access control device is lifted to permit the person to pass from the unrestricted disinfection area through the door access control device to the restricted disinfection area when the person is identified as qualified to pass through the door access control device;

detecting whether a person is intending to pass from the restricted disinfection area through the door access control device to the unrestricted disinfection area;

deciding whether to start a secondary disinfection operation, wherein the secondary disinfection operation is not carried out when any person is in the restricted or unrestricted disinfection area, and wherein the secondary disinfection operation is carried out when the person passing from the restricted area to the unrestricted disinfection area has left the unrestricted disinfection area, wherein the secondary disinfection operation continues until it is completed while no person is in the restricted disinfection area and the unrestricted disinfection area, and wherein the secondary disinfection operation is terminated when completed or any person enters the restricted disinfection area or the unrestricted disinfection area; and identifying whether a primary disinfection operation is completed before lifting the unlocking state of the door access control device, wherein the primary disinfection operation starts during the unlocking judgment procedure and is identified whether completed or not, and wherein the locking state of the door access control device is not lifted before the primary disinfection operation is completed.

2. The door access control method as claimed in claim 1, wherein the primary disinfection operation includes illuminating a first handle of the door access control device with a first handle disinfection device for a period of time.

3. The door access control method as claimed in claim 1, further comprising detecting whether the person passing from the unrestricted disinfection area to the restricted disinfection area has left the restricted disinfection area, wherein the secondary disinfection operation is not carried out when the person is still in the restricted disinfection area, and wherein the secondary disinfection operation is carried out when the person has left the restricted disinfection area.

4. The door access control method as claimed in claim 1, wherein the primary disinfection operation is considered as complete after proceeding for about 5-15 seconds, and wherein the secondary disinfection operation is considered as complete after proceeding for about 10-30 minutes.

5. The door access control method as claimed in claim 1, wherein the secondary disinfection operation includes disinfecting the disinfection area with at least one first disinfection device in the first disinfection area and at least one second disinfection device in the second disinfection area and includes illuminating a first handle of the door access control device with a first handle disinfection device for 1-3 minutes.

* * * * *